(12) United States Patent
Graumann et al.

(10) Patent No.: US 7,401,977 B2
(45) Date of Patent: Jul. 22, 2008

(54) X-RAY APPARATUS WITH COMPONENT POSITIONING COORDINATED WITH RADIO-OPAQUE OBJECTS IN EXAMINATION ROOM

(75) Inventors: Rainer Graumann, Höchstadt (DE); Dieter Ritter, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 14 days.

(21) Appl. No.: 11/485,061

(22) Filed: Jul. 11, 2006

(65) Prior Publication Data
US 2007/0165775 A1 Jul. 19, 2007

(30) Foreign Application Priority Data
Jul. 11, 2005 (DE) .................... 10 2005 032 288

(51) Int. Cl.
*A61B 6/12* (2006.01)

(52) U.S. Cl. ...................... 378/205; 378/197

(58) Field of Classification Search .............. 378/205, 378/196–198, 117, 189
See application file for complete search history.

(56) References Cited

U.S. PATENT DOCUMENTS

2003/0179856 A1* 9/2003 Mitschke et al. ............ 378/205

FOREIGN PATENT DOCUMENTS

DE 36 049 55 A1 2/1986
DE 196 11 705 1/2005

* cited by examiner

*Primary Examiner*—Hoon Song
(74) *Attorney, Agent, or Firm*—Schiff Hardin LLP

(57) ABSTRACT

An x-ray acquisition apparatus has a spatially adjustable x-ray detector, a spatially adjustable x-ray source, and a control unit with which the x-ray source can be aligned relative to the x-ray detector. The control unit accounts for the position of radio-opaque objects in the examination room and, before an x-ray acquisition, outputs a signal is a radio-opaque object is located in the beam path of the x-ray source.

13 Claims, 1 Drawing Sheet

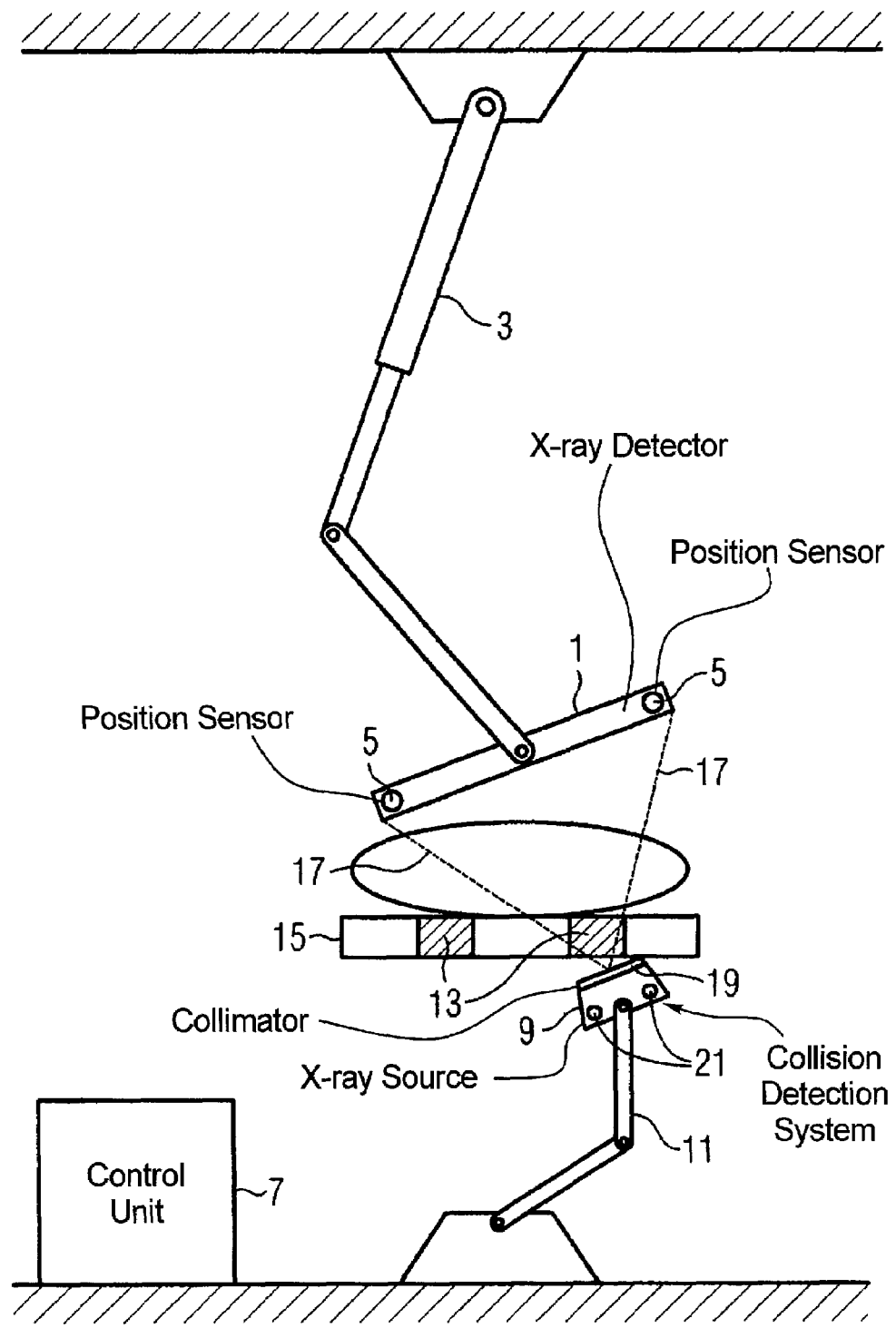

X-RAY APPARATUS WITH COMPONENT POSITIONING COORDINATED WITH RADIO-OPAQUE OBJECTS IN EXAMINATION ROOM

BACKGROUND OF THE INVENTION

1. Field of the Invention

The present invention concerns an x-ray acquisition apparatus of the type having a spatially adjustable x-ray detector, a spatially adjustable x-ray source, and a control unit with which the x-ray source can be aligned to the x-ray detector.

2. Description of the Prior Art

An x-ray acquisition apparatus of this type is known from DE 196 11 705 B4. In the x-ray acquisition apparatus described there, the x-ray source can be aligned relative to the x-ray detector that can be adjusted three-dimensionally in space. This known x-ray acquisition apparatus does not take into account the position of radio-opaque objects that are located in the room (such as perhaps a patient bed that may be located in the beam path). After every positioning of the x-ray detector, therefore, the user must ascertain whether a radio-opaque object is located in the beam path. This assessment represents an additional time expenditure and is not always reliably possible, so that incorrect (flawed) exposures can be created.

SUMMARY OF THE INVENTION

An object of the present invention is to provide an x-ray acquisition apparatus of the aforementioned type in which the desired x-ray imaging (data acquisition) result can be completed in a shorter amount of time.

This object is achieved by an x-ray acquisition apparatus according to the invention having a spatially adjustable x-ray detector, a spatially adjustable source, and a control unit with which the x-ray source can be aligned relative to the x-ray detector, and wherein the control unit takes into account the position of radio-opaque objects located in the room and, before an x-ray acquisition, emit a signal if and when a radio-opaque object is located in the beam path.

As used herein, "radio-opaque object" means an object that strongly absorbs x-ray radiation to an extent that relevant information about the subject to be imaged is lost.

By means of the signal that is emitted as an output from the control unit when a radio-opaque object is located in the beam path, the user is presented in a simple manner with the possibility to change the position of the x-ray detector before an x-ray acquisition is initiated. Incorrect exposures due to radio-opaque objects that are located in the beam path are thereby reliably avoided and the desired x-ray imaging result can be acquired in a shorter amount of time.

In one embodiment, the x-ray detector is manually supported on a mounting device such that the x-ray detector can be adjusted (displaced) three-dimensionally in space. The x-ray source is supported on a further mounting device such that it can be adjusted as well.

At least one sensor with which a detected position of the x-ray detector can be transmitted to the control unit can be located on the x-ray detector. The control unit determines a control signal for the x-ray source with which the x-ray source can be automatically aligned relative to the x-ray detector.

In another embodiment, the position or positions of radio-opaque objects (such as, for example, the position of an operating table) are stored in the control unit and those positions can be compared with the position of the beam path.

The use of further sensors that are attached to the radio-opaque objects is advantageous. The positions of the radio-opaque objects are determined via these sensors and transmitted to the control unit. The position of movable radio-opaque objects during movement thereof thus can also be taken into account.

In a preferred embodiment of the invention, the x-ray acquisition apparatus has a collimator that is controllable via the control unit such that the radiation field of the x-ray source is limited and matched to the size of the x-ray detector. The manual set-up step in which the collimator is adjusted is thus omitted. The acquisition can be executed without time delay.

The position detection of the x-ray detector can be implemented using acoustic and/or optical and/or electromagnetic sensors.

The mounting device on which x-ray source is mounted preferably is equipped with a collision detection system so that collisions with objects or people are avoided during movement of the x-ray source towards the x-ray detector.

In another embodiment, a further signal can be generated that informs the user if and when the x-ray source cannot be aligned relative to the x-ray detector, for example when an object prevents the alignment of the x-ray source relative to the x-ray detector. In this case, the user is informed by the further signal so that he or she can take measures in order to correct the problem, perhaps by removal of the interfering object or by a repositioning of the x-ray detector.

The x-ray acquisition apparatus is appropriately equipped with a control unit that is executed as a computer. In addition to its functions, the computer can produce tomosynthesis images or 3D image reconstructions from a number of exposures of the subject from different positions. Naturally, however, separate computers or computer modules can be used to perform the respective functions of control and image generation.

The mounting device of the x-ray source and/or of the x-ray detector can be a robot arm with six degrees of freedom. Such a robot allows a large freedom of movement with a space-saving design.

DESCRIPTION OF THE DRAWING

The single figure schematically illustrates an x-ray apparatus constructed and operating in accordance with the principles of the present invention.

DESCRIPTION OF THE PREFERRED EMBODIMENTS

The drawing shows a ceiling-mounted x-ray detector 1 that can be three-dimensionally adjusted in space with a manually adjustable mounting arm 3 with six degrees of freedom. Sensors 5 are located on the x-ray detector 1 that supply signals to a control unit 7 that calculates therefrom the spatial position of the x-ray detector 1. An x-ray source 9 is adjustable in a motorized manner in space by a robot arm 11 with six degrees of freedom and is aligned relative to the x-ray detector 1 by control signals from the control unit 7. The spatial positions of radio-opaque objects such as, for example, radio-opaque parts 13 of the operating table 15 are stored in the control unit 7. If a radio-opaque object 13 is located in the beam path 17 (as is shown in the drawing), a signal that informs the user about this situation is output by the control unit 7. The user can thereupon reposition the x-ray detector 1.

A collimator 19 is located on the x-ray source 9 that is automatically controlled by the control unit. 7 to adjust the aperture angle of the beam path 17 to match the x-ray detector A high image performance can be realized by a fixed installation of the x-ray acquisition apparatus.

A collision detection system 21 is located on the x-ray source 9 that avoids collision of the x-ray source with people or objects during the motorized alignment of the x-ray source 9. If the x-ray source 9 cannot be aligned relative on the x-ray detector 1 (because, for example, an object prevents this), a further signal is output that informs the user about this situation. The x-ray detector 1 can thereupon be repositioned.

In the exemplary embodiment, the control unit 7 is fashioned as a computer. Since the spatial position of the x-ray detector 1 is detected during an acquisition of image data, three-dimensional image reconstructions and tomosynthesis images can be produced from a number of exposures from different directions. The produced images can be shown to the user at monitors that are hung from the ceiling or are located on a monitor cart.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray apparatus comprising:
    a spatially adjustable x-ray source that emits x-rays in a beam path;
    a spatially adjustable x-ray detector; and
    a control unit connected to said x-ray source and to said x-ray detector that aligns said x-ray source relative to said x-ray detector so that said x-ray detector is in said beam path to acquire diagnostic data from a subject between the x-ray source and the x-ray detector, said control unit identifying a position of a radio-opaque object in an examination room in which said x-ray source and said x-ray detector are located that blocks at least part of said beam path from reaching said x-ray detector that would otherwise be used to acquire diagnostic data from the subject and that, before acquiring diagnostic data from the subject with said x-ray source and said x-ray detector, emits a humanly perceptible signal if and when the radio-opaque object is located in the beam path.

2. An x-ray apparatus as claimed in claim 1 comprising a mounting device for said x-ray detector, said mounting device allowing manual, three-dimensional adjustment in space of said x-ray detector.

3. An x-ray apparatus as claimed in claim 2 wherein said mounting device is a robot arm.

4. An x-ray apparatus as claimed in claim 1 comprising a motorized mounting device for said x-ray source, operated by said control unit, allowing motorized adjustment in space of said x-ray source.

5. An x-ray apparatus as claimed in claim 4 comprising a sensor that detects a position of the x-ray detector and that is in communication with said control unit to supply a signal to the control unit representing said detected position, and wherein said control unit generates a control signal that operates said motorized mounting device for said x-ray source to automatically align said x-ray source relative to said x-ray detector so that said radio-opaque object is not located in said beam path.

6. An x-ray apparatus as claimed in claim 5 wherein said sensor is a sensor selected from the group consisting of acoustic sensors, optical sensors and electromagnetic sensors.

7. An x-ray apparatus as claimed in claim 5 wherein said motorized mounting device is a motorized robot arm.

8. An x-ray apparatus as claimed in claim 5 comprising a collision detection system associated with said x-ray source that avoids collision of said x-ray source with people and objects during movement of said x-ray source.

9. An x-ray apparatus as claimed in claim 8 wherein said collision detection system is in communication with said control unit, and wherein said control unit emits a further humanly perceptible signal if said x-ray source cannot be aligned relative to said x-ray detector.

10. An x-ray apparatus as claimed in claim 1 wherein said control unit comprises a memory in which respective spatial positions in the examination room of radio-opaque objects in the examination room are stored.

11. An x-ray apparatus as claimed in claim 2 comprising a sensor mounted on a radio-opaque object in the examination room, said sensor being in communication with said control unit and supplying a signal to the control unit indicating a position in the examination room of the radio-opaque object, and wherein said control unit generates a control signal that operates said motorized mounting device for said x-ray source to automatically align said x-ray source relative to said x-ray detector so that said radio-opaque object is not located in said beam path.

12. An x-ray apparatus as claimed in claim 1 comprising a collimator disposed at said x-ray source in said beam path, said collimator being in communication with and controlled by said control unit to limit a radiation field emitted by said x-ray source to match a size of said x-ray detector.

13. An x-ray apparatus as claimed in claim 1 wherein said control unit is a computer, and wherein said computer generates an image, selected from the group consisting of tomosynthesis images and 3D reconstructed images, from image data acquired by said x-ray detector.

* * * * *